(12) United States Patent
Vanoppen et al.

(10) Patent No.: US 7,408,086 B2
(45) Date of Patent: Aug. 5, 2008

(54) NI/TIO$_2$ HYDROGENATION CATALYST

(75) Inventors: Dominic Vanoppen, Kapellen (BE); Ekkehard Schwab, Neustadt (DE); Joern Mueller, Bad Essen (DE); Ulrich Penzel, Tettau (DE); Gunter Georgi, Baton Rouge, LA (US); Bernd Weidner, Wormlage (DE); Dietrich Tittelbach-Helmrich, Tauscha (DE); Juergen Dahlhaus, Bruessel (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 583 days.

(21) Appl. No.: 10/478,475

(22) PCT Filed: May 16, 2002

(86) PCT No.: PCT/EP02/05423

§ 371 (c)(1),
(2), (4) Date: Nov. 21, 2003

(87) PCT Pub. No.: WO02/094434

PCT Pub. Date: Nov. 28, 2002

(65) Prior Publication Data

US 2004/0147783 A1 Jul. 29, 2004

(30) Foreign Application Priority Data

May 21, 2001 (DE) ................. 101 24 600

(51) Int. Cl.
C07C 29/36 (2006.01)
B01J 23/00 (2006.01)

(52) U.S. Cl. ................. 564/422; 502/302; 502/303; 502/304; 502/328; 502/335; 502/337; 502/350; 502/351

(58) Field of Classification Search ......... 502/326–328, 502/330–332, 335, 337, 350, 439, 315, 302–304, 502/351; 564/422
See application file for complete search history.

(56) References Cited

U.S. PATENT DOCUMENTS

| 2,866,752 | A | * | 12/1958 | Zimmerschied et al. ..... 208/217 |
|---|---|---|---|---|
| 2,889,286 | A | * | 6/1959 | Faulkner ................... 502/242 |
| 3,533,963 | A | * | 10/1970 | Gignier et al. ............. 502/306 |
| 3,794,588 | A | | 2/1974 | Stiles |
| 3,868,332 | A | | 2/1975 | Carter et al. |
| 3,972,829 | A | * | 8/1976 | Michalko ................... 502/230 |
| 4,042,615 | A | * | 8/1977 | Vannice et al. ............. 518/715 |
| 4,073,750 | A | * | 2/1978 | Yates et al. ................ 502/259 |
| 4,113,658 | A | * | 9/1978 | Geus ........................ 502/242 |
| 4,160,745 | A | * | 7/1979 | Murrell et al. ............. 502/185 |
| 4,188,333 | A | * | 2/1980 | Cahen ........................ 554/145 |
| 4,273,724 | A | * | 6/1981 | Kugler et al. ............... 518/715 |
| 4,536,482 | A | * | 8/1985 | Carcia ............................ 502/5 |
| 4,537,873 | A | * | 8/1985 | Kato et al. .................. 502/242 |
| 4,977,126 | A | * | 12/1990 | Mauldin et al. ............. 502/242 |
| 5,095,160 | A | * | 3/1992 | Penella et al. .............. 585/476 |
| 5,100,858 | A | * | 3/1992 | Chopin et al. .............. 502/350 |
| 5,204,309 | A | * | 4/1993 | Vorob'iev et al. .......... 502/306 |
| 5,552,363 | A | * | 9/1996 | Pannell et al. .............. 502/337 |
| 5,977,013 | A | * | 11/1999 | Elliott et al. ................ 502/337 |
| 6,037,289 | A | * | 3/2000 | Chopin et al. .................. 502/2 |
| 6,191,067 | B1 | * | 2/2001 | Koike et al. ................. 502/350 |
| 6,235,677 | B1 | * | 5/2001 | Manzer et al. .............. 502/232 |
| 6,309,758 | B1 | * | 10/2001 | Schmidt ...................... 428/570 |
| 6,362,121 | B1 | * | 3/2002 | Chopin et al. .................. 502/2 |
| 6,444,608 | B1 | * | 9/2002 | Oki et al. .................... 502/300 |
| 6,524,994 | B1 | * | 2/2003 | Reesink et al. .............. 502/337 |
| 6,528,029 | B1 | * | 3/2003 | Dettling et al. ............. 423/210 |
| 6,842,512 | B2 | * | 1/2005 | Pedersen ................. 379/142.01 |
| 6,964,826 | B2 | * | 11/2005 | Ovshinsky et al. ............ 429/44 |
| 7,045,484 | B2 | * | 5/2006 | Fetcenko et al. ............. 502/300 |
| 2001/0049335 | A1 | * | 12/2001 | Kitchen et al. .............. 502/305 |
| 2002/0052289 | A1 | * | 5/2002 | Manzer et al. ................ 502/66 |
| 2003/0050188 | A1 | * | 3/2003 | Ovshinsky et al. .......... 502/300 |
| 2005/0120827 | A1 | * | 6/2005 | Fetcenko et al. .............. 75/370 |

FOREIGN PATENT DOCUMENTS

| DE | 152 065 | 11/1981 |
|---|---|---|
| DE | 284 371 | 11/1990 |
| DE | 199 09 168 | 9/2000 |
| DE | 199 09 176 | 9/2000 |
| DE | 199 09 177 | 9/2000 |
| DE | 199 15 357 | 10/2000 |
| DE | 199 22 038 | 11/2000 |
| EP | 1 163 955 | 12/2001 |
| FR | 2 347 326 | 11/1977 |
| WO | 95/14647 | 6/1995 |

OTHER PUBLICATIONS

Russian Journal of Applied Chemistry, vol. 70, No. 8, pp. 1236-1253 1997.

* cited by examiner

*Primary Examiner*—Cam N. Nguyen
(74) *Attorney, Agent, or Firm*—Oblon, Spivak, McClelland, Maier & Neustadt, P.C.

(57) ABSTRACT

A catalyst comprising nickel on a TiO$_2$ support is obtainable by coprecipitation of
  nickel and
  at least one further metal selected from among Si, Zr, Hf, alkaline earth metals, Y, La and Ce, and
  optionally at least one dopant metal selected from groups 5 to 11 of the Periodic Table of the Elements,
  from a solution in which the corresponding metal salts are present onto a particulate TiO$_2$ support, subsequent drying, calcination and reduction and optionally passivation to give the nickel-containing catalyst.

It is used, in particular, for the hydrogenation of nitroaromatic compounds.

8 Claims, No Drawings

NI/TIO₂ HYDROGENATION CATALYST

BACKGROUND OF THE INVENTION

The present invention relates to a hydrogenation catalyst which comprises nickel on a $TiO_2$ support. The catalyst is used particularly for the hydrogenation of nitroaromatic compounds to form the corresponding aromatic amino compounds.

The use of nickel-containing catalysts as hydrogenation catalysts has been known for a long time. In Russian Journal of Applied Chemistry, Vol. 70, No. 8, 1997, pages 1236 to 1253, the preparation of such nickel-containing catalysts is described in detail. The catalysts described comprise nickel predominantly on silicon dioxide or aluminum oxide as support.

They can be prepared by precipitation onto the support or by coprecipitation. Use is also made of $SiO_2/TiO_2$ supports, and it is indicated that $TiO_2$ as modifier can lead to mechanically stable catalysts.

DD-A-152 065 relates to a process for the hydrogenation of nitroaromatics using stirring-stable suspension catalysts. The catalyst is prepared by precipitation of a nickel salt solution in the presence of silica gel having a particular particle size distribution.

DD-A-284 371 relates to a process for the reduction of nitroaromatics in the presence of an $Ni/SiO_2$ catalyst. The catalyst is supported on a support having a size of more than 1 mm and is passivated after activation. Prior to the reaction, the catalyst is milled in the reactor.

U.S. Pat. No. 3,868,332 relates to a hydrogenation catalyst which is used, in particular, for the conversion of benzene into cyclohexane. The catalyst is prepared by coprecipitation of nickel and silicate ions in the presence of a porous silicon dioxide support.

WO 95/14647 relates to a process for the oligomerization of olefins to form highly linear oligomers. The process is carried out using an oxidic catalyst comprising nickel oxide, silicon dioxide and titanium dioxide and also an alkali metal oxide. The catalyst is prepared by coprecipitation of a nickel salt solution onto finely divided titanium dioxide powder by means of a sodium water glass solution. Nickel is present in oxidic form, and the catalyst is used in the form of pressed pellets as a fixed bed. Use as hydrogenation catalyst is not described.

DE-A-199 09 176 and DE-A-199 09 168 relate to hydrogenation catalysts comprising nickel and frequently zirconium on a zirconium-containing support.

In the hydrogenation of nitroaromatic compounds to form aromatic amino compounds, the catalyst is exposed to a strongly alkaline medium. A catalyst dispersed in the reaction medium is subjected to high mechanical stresses when the reaction mixture is circulated or stirred. It should have a particle size distribution such that it can be both readily dispersed and readily separated off under operating conditions.

SUMMARY OF THE INVENTION

It is an object of the present invention to provide a catalyst for the hydrogenation of nitroaromatic compounds which displays the property profile mentioned above and avoids the disadvantages of the known catalysts.

We have found that this object is achieved by a catalyst comprising nickel on a $TiO_2$ support and obtainable by coprecipitation of nickel and
at least one further metal selected from among Si, Zr, Hf, alkaline earth metals, Y, La and Ce, and
optionally at least one dopant metal selected from groups 5 to 11 of the Periodic Table of the Elements,
from a solution in which the corresponding metal salts are present onto a particulate $TiO_2$ support, subsequent drying, calcination and reduction and optionally passivation to give the nickel-containing catalyst.

DETAILED DESCRIPTION OF THE INVENTION

According to the present invention, it has been found that coprecipitation of nickel and another support precursor metal in oxide form onto a $TiO_2$ support gives particulate catalysts which are not only chemically stable in a strongly alkaline medium but are also physically stable when subjected to severe mechanical stress, for example by means of a circulation pump. Use of customary particulate $TiO_2$ supports as starting materials gives particulate catalysts which, under operating conditions, are both readily dispersed and readily separated off and allow good material transport.

In addition, the coprecipitation of nickel and a further support precursor allows an advantageous particle size distribution of the catalyst and the formation of small nickel crystallites which lead to a high activity of the catalyst.

The mean particle size ($d_{50}$) of the catalyst is preferably at least 3 µm, particularly preferably at least 4 µm, in particular at least 5 µm. It is preferably not more than 80 µm, particularly preferably not more than 40 µm.

The nickel crystallite size, determined by XRD, is preferably at least 4 nm, particularly preferably at least 7 nm. It is preferably not more than 20 nm, particularly preferably not more than 15 nm. A special preference is given to ranges from 7 to 15 nm and, in particular, from 10 to 12 nm. These crystallite sizes allow a high activity of the catalyst, while the crystallites are still able to be passivated on their surface to make it possible to handle the catalyst in air. At smaller particle sizes, the crystallites are more easily oxidized right through during passivation. Larger crystallite sizes reduce the activity of the catalyst for a given amount of nickel.

The proportion of nickel in the catalyst of the present invention is preferably from 20 to 80% by weight, particularly preferably from 40 to 70% by weight, in particular from 50 to 65% by weight, based on the total catalyst and based on nickel as metal.

The weight ratio of the oxide of the further metal or metals to the $TiO_2$ support is preferably (0.2-4):1, particularly preferably (0.5-2):1, in particular (0.8-1.2):1. Most prefera similar amounts of $TiO_2$ support and oxide of the further metal or metals (other support precursor) are used.

If at least one dopant metal is used, its amount is, based on the oxide and the total catalyst, from 0.1 to 10% by weight, particularly preferably from 1 to 7% by weight.

The catalysts of the present invention display a high mechanical stability, so that although they do experience a reduction in particle size during use as dispersed catalyst, the particle size remains in a range which allows the catalyst to be separated off by means of a settler.

Sedimentation by means of a settler simplifies the separation of the catalyst from the reaction mixture and the subsequent reuse of the catalyst.

If small amounts of the catalyst form particles smaller than the preferred particle size during the course of the process, this is not a problem since catalyst consumed in this way can be discharged from the reaction system since it is not retained in the settler.

The specific support combination in particular gives the catalyst of the present invention its advantageous property profile.

It is also possible to passivate the catalyst of the present invention after reduction in order to make it possible for it to be stored and easily handled in air. On this subject reference may be made, for example, to DE-A-199 09 175.

During preparation of the catalyst, it can be subjected to one or more shaping steps. For example, it is possible for the catalyst to be, after precipitation and drying, brought to a desired shape before or after calcination, to be reduced, to be passivated and then to be converted into catalyst particles of the desired particle size. The precipitated catalyst precursor can, for example, be filtered off from the precipitation solution and dried, after which lumps of the filter cake are calcined, reduced, passivated and milled again. Other possible shaping steps are tableting and extrusion.

The preparation of the catalyst of the present invention by precipitation is preferably carried out as follows:

$TiO_2$ powder (for example S 150 from Kemira) is milled to a particle diameter of <100 µm, added to water and dispersed for 5 minutes by means of an Ultraturrax. If it is to be used, water glass is now added as Si source. The pH is adjusted to a value in the range from 5 to 10, a solution of nickel nitrate and, if desired, additional salts such as zirconium acetate, cerium nitrate and/or magnesium nitrate is pumped in over a period of 30 minutes, during which time the pH is kept constant at a value in the range from 5 to 10 by simultaneously pumping in a sodium carbonate solution and, if desired, a water glass solution. The mixture is then stirred for 30 minutes while air is blown into it. The pH is brought to a value of at least 7.5 by means of sodium carbonate solution. The precipitated product is filtered off and washed until it is free of nitrate. The filter cake is dried (12 hours, 120° C.) and subsequently calcined (4 hours, 400° C.). The product obtained in this way is comminuted to a mean particle diameter of <100 µm and reduced for 4 hours at from 400 to 550° C. in a stream of hydrogen.

The invention also provides a process for preparing a catalyst as defined above, in which the process steps indicated are carried out.

In addition, the invention provides for the use of the catalyst for the hydrogenation of nitroaromatic compounds.

The invention also provides a process for preparing aromatic amino compounds by hydrogenation of corresponding nitroaromatic compounds, in which the hydrogenation is carried out in the presence of a catalyst as defined above.

In this process, it is possible to use any nitroaromatic compounds. The nitroaromatic compounds are preferably selected from among nitrobenzene, nitrotoluene and dinitrotoluene. Corresponding aromatic amino compounds which can be prepared are aniline, o-toluidine, p-toluidine and toluenediamine.

The hydrogenation of the present invention can be carried out continuously or batchwise in the liquid phase or the gas phase. It is preferably carried out in the liquid phase. The reaction can be carried out in the presence of a suitable solvent.

The hydrogenation is particularly preferably carried out in a dispersion of the catalyst.

The hydrogenation is preferably carried out at from 60 to 200° C., particularly preferably from 100 to 140° C., and a hydrogen pressure of from 5 to 100 bar, particularly preferably from 20 to 30 bar.

For a description of the process conditions, reference may also be made to DE-A-199 09 168.

The invention is illustrated below with the aid of examples.

EXAMPLES

The preparation of the catalysts was carried out as described above in the general method of preparation. Zr was used as acetate, Si was used as water glass, $TiO_2$ was used as powder and the other metals were used as nitrates. The coprecipitation was carried out at the pH values specified in Table 1, which were, if necessary, set by addition of sodium carbonate solution. The mixture was then stirred for 1 hour at room temperature while blowing air into it, after which the pH was, if necessary, set to 7.5 by addition of sodium carbonate solution. After the precipitate had been filtered off with suction and washed with water to remove nitrate, it was dried at 120° C. for 12 hours, optionally pressed through a 1 mm sieve, and reduced at from 350 to 550° C. for 4 hours and passivated.

The catalysts prepared by the above method were examined by means of XRD to determine the nickel crystallite size. In addition, the $d_{50}$ was determined from the particle size distribution. This can be achieved, for example, in a Sympatec-Helos suspension cell using water containing 1 g/l of sodium pyrophosphate as dispersion medium. To determine the mechanical stability of the catalysts, they were milled in an Ultraturrax for 1, 3 or 10 minutes. If reduction was carried out at different temperatures, the temperatures are indicated. The results are summarized in Table 1 below.

TABLE 1

Catalysts prepared by coprecipitation together with the pH at which precipitation was carried out, the Ni crystallite size (XRD) and the $d_{50}$ of the particle size distribution after milling in an Ultraturrax for 1/3/10 minutes.

| Cat. | Preparation | Ni (nm) | $d_{50}$ (µm) |
|---|---|---|---|
| 1 | Precipitation of 50% Ni onto 25% $ZrO_2$/25% $TiO_2$ RT, pH 5.7 | 14 | (350° C.)8/6.4/4.6, (450° C.) 8.1/6.4/5.7 |
| 2 | Precipitation of 50% Ni onto 15% $ZrO_2$/35% $TiO_2$ RT, pH 5.7 | 21 | 7.5/4.5/3 |
| 3 | Precipitation of 50% Ni onto 25% $TiO_2$/25% $ZrO_2$, pH 5 | | 8/6/3.5 |
| 4 | Precipitation of 50% Ni onto 45% $TiO_2$ + 5% $Ce_2O_3$, pH 6 | 12.5 | 7.3/4/3.7 |
| 5 | Precipitation of 50% Ni onto 25% $TiO_2$ + 25% MgO, pH 9 | 18.5 | 18/7.5/3.7 |
| 6 | Precipitation of 50% Ni onto 25% $TiO_2$ + 25% MgO, pH 10 | 6.0 | 18/12.5/3.4 |
| 7 | Precipitation of 50% Ni onto 25% $TiO_2$ + 25% $SiO_2$, pH 6 | 4.5 | |
| 8 | Precipitation of 50% Ni onto 25% $TiO_2$ + 25% $SiO_2$, pH 9 | 5.0 | 43/40/13 |
| 9 | Precipitation of 50% Ni onto 25% $TiO_2$ + 25% $SiO_2$, pH 6 | 5.5 | 55/40/17 |
| 10 | Precipitation of 50% Ni onto 25% $TiO_2$ + 25% $MgO:SiO_2$, pH 9 | 6.5 | 30/25/15 |
| 11 | Precipitation of 50% Ni onto 25% $TiO_2$ + 25% $MgO:SiO_2$, pH 10 | 6.0 | 42/33/20 |
| 12 | Precipitation of 50% Ni onto 25% $TiO_2$ + 25% $MgO:ZrO_2$, pH 9 | 9.5 | 18/14/3.4 |
| 13 | Precipitation of 50% Ni onto 25% $TiO_2$ + 25% $MgO:ZrO_2$, pH 10 | 6.0 | 36/31/8 |
| 14 | Precipitation of 50% Ni + 15% $ZrO_2$ + 5% $Ce_2O_3$ onto 30% $TiO_2$, pH 5.7 | 10 | 4.4/4.1/3.8 |
| 15 | Precipitation of 50% Ni + 25% $SiO_2$ onto 25% $TiO_2$, pH 5.7 | 5.5 | 10.6/8.8/3.0 |
| 16 | Precipitation of 50% Ni + 5% Fe + 22.5% $MgO:SiO_2$ onto 22.5% $TiO_2$, pH 9 | 6 | 29/18/10 |
| 17 | Precipitation of 50% Ni + 5% Fe + 22.5% $ZrO_2$ onto 22.5% $TiO_2$, pH 5.6 | 15 | 7.6/6.6/5.6 |

TABLE 1-continued

Catalysts prepared by coprecipitation together with the pH at which precipitation was carried out, the Ni crystallite size (XRD) and the $d_{50}$ of the particle size distribution after milling in an Ultraturrax for 1/3/10 minutes.

| Cat. | Preparation | Ni (nm) | $d_{50}$ (μm) |
|---|---|---|---|
| 18 | Precipitation of 70% MgO:SiO$_2$ onto 15% TiO$_2$, pH 9 | 6.5 | 7.4/4.4/3 |
| C1 | Precipitation of 50% Ni onto 50% TiO$_2$, pH 5.6 | 54 | 5.6/4.8/4.3 |

RT: room temperature

In each case, the components other than TiO$_2$ were precipitated onto TiO$_2$. The percentages eight of oxide, except for Ni where they refer to the weight of metal.

The catalysts were used for the hydrogenation of dinitrotoluene (DNT) to form toluenediamine (TDA). This was carried out as follows:

A 300 ml autoclave was charged with 0.8 g of a freshly reduced catalyst, 100 ml of n-butanol and 20 g of DNT, pressurized with hydrogen to 25 bar and heated to 80° C. The hydrogen uptake in l/min was taken as a measure of the activity.

The results of the hydrogenation experiments are summarized in Table 2.

TABLE 2

Hydrogenation experiments (80° C., 25 bar, 10 ml of n-butanol, 20 g of DNT, 0.8 g of catalyst, 3 h)

| Cat. | Conversion (5) | TDA yield (%) | H$_2$ uptake (l/min) |
|---|---|---|---|
| 1 | 100 | 96.76 | 0.10 |
| 2 | 100 | 97.64 | 0.40 |
| 7 | 100 | 98.78 | 0.70 |
| 8 | 100 | 99.03 | 0.48 |
| 9 | 100 | 99.11 | 0.37 |
| 10 | 100 | 97.35 | 0.40 |
| 11 | 100 | 98.09 | 0.67 |
| 12 | 100 | 97.77 | 0.12 |
| 13 | 100 | 97.79 | 0.17 |
| 14 | 100 | 99.21 | 0.23 |
| 15 | 100 | 97.58 | 0.75 |
| 16 | 100 | 98.6 | 2.00 |
| 17 | 100 | 96.82 | 0.28 |
| 18 | 100 | 99 | 0.53 |
| C1 | 100 | 99.48 | 0.13 |

The results show that the catalysts of the present invention display an advantageous combination of activity and mechanical stability.

The invention claimed is:

1. A catalyst, comprising:
   nickel on a TiO$_2$ support;
   wherein the catalyst is prepared by:
   co-precipitating:
      nickel;
      at least one further metal selected from the group consisting of alkaline earth metals, Y, La and Ce; and
      optionally at least one dopant metal selected from the group consisting of elements of groups 5 to 11 of the Periodic Table of the Elements;
   onto a particulate TiO$_2$ support from a solution in which corresponding metal salts are included; and
      subsequently drying, calcining, reducing, and optionally passivating the support to obtain the catalyst;
   wherein the catalyst has a mean particle size ($d_{50}$) of from 3 to 80 μm.

2. A catalyst as claimed in claim 1, wherein the catalyst comprises nickel in an amount of from 20 to 80% by weight, based on a total weight of the catalyst.

3. A catalyst as claimed in claim 1, wherein a weight ratio of an oxide of the further metal or metals to the TiO$_2$ support is from 0.2:1 to 4:1.

4. A catalyst as claimed in claim 1, wherein:
   preparing the catalyst further comprises forming nickel crystallites; and
   the nickel crystallites are from 4 to 20 nm in size.

5. A catalyst as claimed in claim 1, wherein preparing the catalyst comprises performing passivating after performing reducing.

6. A process for preparing a catalyst as claimed in claim 1, comprising:
   co-precipitating:
      nickel;
      at least one further metal selected from the group consisting of alkaline earth metals, Y, La and Ce; and
      optionally at least one dopant metal selected from the group consisting of elements of groups 5 to 11 of the Periodic Table of the Elements;
   onto a particulate TiO$_2$ support from a solution in which corresponding metal salts are included; and
      subsequently drying, calcining, reducing, and optionally passivating the support to obtain the catalyst.

7. A process for preparing aromatic amino compounds, comprising:
   hydrogenating nitroaromatic compounds in the presence of a catalyst as defined in claim 1.

8. A process as claimed in claim 7, wherein the aromatic amino compounds are selected from the group consisting of aniline, o-toluidine, p-toluidine and toluenediamine.

* * * * *